Sept. 24, 1974
F. W. ANDERSON
PEAR TREE
Filed Aug. 23, 1973
Plant Pat. 3,622
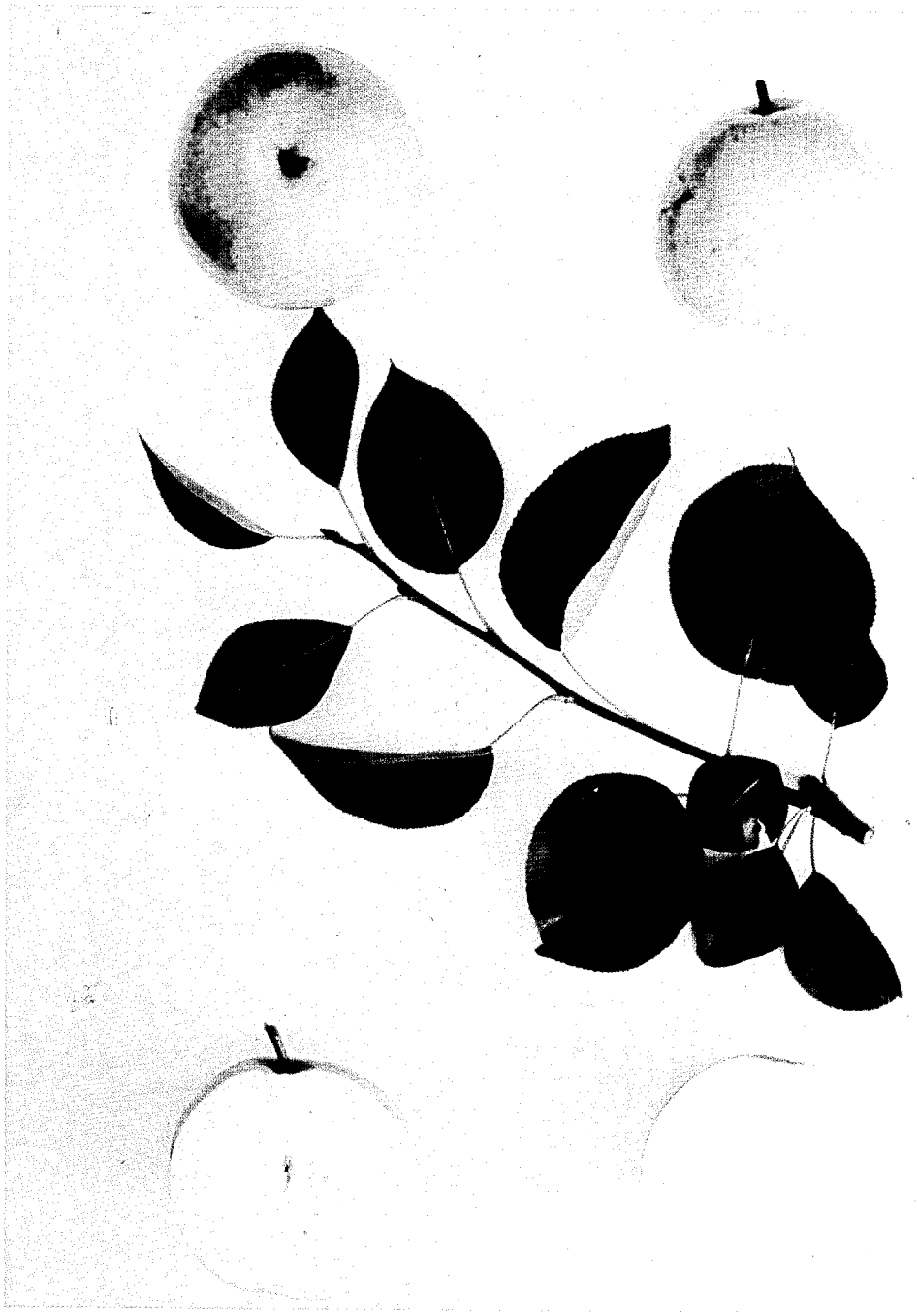

United States Patent Office

Plant Pat. 3,622
Patented Sept. 24, 1974

3,622
PEAR TREE
Frederic W. Anderson, 826 W. 22nd St.,
Merced, Calif. 95340
Filed Aug. 23, 1973, Ser. No. 391,157
Int. Cl. A01h 5/03
U.S. Cl. Plt.—36 1 Claim

ABSTRACT OF THE DISCLOSURE

A pear tree which is of medium size, vigorous, spreading, tall, rapid growing, foliated with medium size, obovate leaves having a finely serrate margin, and a regular and very productive bearer of large, uniform, round-to-oblate, symmetrical fruit having yellow-green skin lightly blushed with red on the sunny side, and substantially white, semi-translucent flesh.

Background of the variety: Over a substantial number of years I have engaged in an extensive and continuing plant breeding program at my experimental nursery and orchard located near Le Grand, Merced County, Calif.; one purpose of such program being to provide improved varieties of fruit trees. The present variety of pear tree resulted from my endeavors in the conduct of such plant breeding program.

Origin of the variety: The present variety of pear tree was originated by me, in my aforesaid experimental nursery and orchard, as an open-pollinated seedling of a Max-Red Bartlett (United States Plant Pat. No. 741). More particularly, three Korean pear trees were growing adjacent to the Max-Red Bartlett tree, and—from the appearance of the tree, leaves, and fruit of such seedling thereof—it is probable that the present variety is a natural cross between one of such Korean pears and the Max-Red Bartlett.

Asexual reproduction of the variety: Subsequent to recognition by me of certain novel and distinctive characteristics—as will hereinafter appear—of the present variety of pear tree, I asexually reproduced it by grafting on mature orchard trees in my said experimental orchard. In maturity, such reproductions ran true to the original seedling tree in all respects.

Summary of the variety: The present variety of pear tree is of medium size, vigorous, spreading, tall, rapid growing, foliated with medium size, obovate leaves having a finely serrate margin, and a regular and very productive bearer of large, uniform, round-to-oblate, symmetrical fruit having yellow-green skin lightly blushed with red on the sunny side, and substantially white, semi-translucent flesh; the variety blooming a few days before the Bartlett (unpatented), and ripening two to three weeks later than the Bartlett.

The present variety of pear tree bears fruit which—because of its round to oblate form—is, distinctively, more of the shape of many apples, and hence not the shape of the Bartlett and most other European-type pears.

Additionally, the present variety of pear tree bears fruit which not only keep and ship well, but are of excellent eating quality enhanced by crisp, tender, juicy flesh having a most agreeable flavor; the flesh being further characterized by the absence of undesirable grit cells as are present, for example, in the flesh of the Kieffer (unpatented).

Brief description of the drawing: The drawing is an illustration, by photographic reproduction in color, of a twig with leaves, and separate fruit; one of the latter being cut into halves to expose the flesh.

Description of the variety: The botanical details of this new and distinct variety of pear tree—with color definitions (except those in common color terms) referenced to Maerz and Paul Dictionary of Color—are as follows:

Tree
- *Size.*—Medium.
- *Vigor.*—Vigorous.
- *Form.*—Spreading, Tall.
- *Growth.*—Rapid.
- *Production.*—Very productive.
- *Bearing.*—Regular bearer.

Trunk
- *Size.*—Medium.
- *Texture.*—Medium.

Branches
- *Size.*—Medium.
- *Color.*—Brown.
- *Lenticels.*—Number: Medium, size: medium.

Leaves
- *Size.* — Medium. Average length—3". Average width—2½".
- *Form.*—Obovate.
- *Thickness.*—Thick.
- *Texture.*—Smooth.
- *Margin.*—Finely serrate.
- *Petiole.*—Medium length—average 1½". Medium thickness.
- *Color.*—Top side—Dark green (24–L–7). Under side—Lighter yellowish green (21–J–6).

Flowers
- *Blooming Period.*—2 or 3 days before Bartlett.

Fruit
- *Ripening Period.*—About with Anjou pear (unpatented).
- *Length of Season.*—Long.
- *Retention.*—Hangs well.
- *Size.*—Large. Average diameter axially—2¾". Average transversely—3". Uniform.
- *Form.*—Round to oblate. Symmetrical. Uniform.
- *Stem.*—Short—average ½". Medium thickness.
- *Cavity.*—Shallow. Broad.
- *Lobes.*—Medium length. Medium breadth.

Skin
- *Thickness.*—Medium.
- *Texture.*—Smooth. Glossy.
- *Color.*—Yellowish green (20–K–3) lightly blushed on the sunny side with red (5–K–8).
- *Dots.*—Numerous. Medium size. Russet.

Flesh
- *Color.*—White (9–B–1). Semi-translucent.
- *Texture.*—Fine. Crisp. Tender. Juicy.
- *Flavor.*—Subacid. Sprightly.
- *Eating Quality.*—Very good.
- *Core.*—Medium size. Closed.
- *Calyx Tube.*—Length: Medium. Width: Medium.
- *Seed.*—Size: Medium. Form: Plump.

Use
- Dessert. Local and long distance market.

Keeping quality: Good.

Resistance to insects and diseases: No unusual susceptibilities noted.

Shipping quality: Good.

The pear tree and its fruit herein described may vary in slight detail due to climatic and soil conditions under which the variety may be grown; the present description being of the variety as grown in the Central Valley of California.

I claim:

1. A new and distinct variety of pear tree, substantially as illustrated and described, which is of medium size, vigorous, spreading, tall, rapid growing, foliated with medium size, obovate leaves having a finely serrate margin, and a regular and very productive bearer of large, uniform, round-to-oblate, symmetrical fruit having yellow-green skin lightly blushed with red on the sunny side, and substantially white, semi-translucent flesh; the variety blooming a few days before the Bartlett, ripening two to three weeks later than the Bartlett; the generally "apple-shaped" fruit keeping and shipping well, and being of excellent eating quality enhanced by crisp, tender, juicy flesh having an agreeable flavor and an absence of grit cells.

No references cited.

ROBERT E. BAGWILL, Primary Examiner